(12) United States Patent
Sakuta

(10) Patent No.: US 9,719,949 B2
(45) Date of Patent: Aug. 1, 2017

(54) X-RAY FLOURESCENT ANALYZER

(71) Applicant: Hitachi High-Tech Science Corporation, Minato-ku, Tokyo (JP)

(72) Inventor: Masahiro Sakuta, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 72 days.

(21) Appl. No.: 14/792,706

(22) Filed: Jul. 7, 2015

(65) Prior Publication Data

US 2016/0011129 A1 Jan. 14, 2016

(30) Foreign Application Priority Data

Jul. 8, 2014 (JP) ................... 2014-140234

(51) Int. Cl.
*G01N 23/223* (2006.01)
*G01N 23/22* (2006.01)
*G01N 35/00* (2006.01)
*G01T 7/12* (2006.01)

(52) U.S. Cl.
CPC ....... *G01N 23/223* (2013.01); *G01N 23/2204* (2013.01); *G01N 35/00693* (2013.01); *G01N 35/00732* (2013.01); *G01T 7/12* (2013.01); *G01N 2035/00702* (2013.01)

(58) Field of Classification Search
CPC ..... G01N 2035/00702; G01N 23/2204; G01N 23/223; G01N 35/00693; G01N 35/00732; G01N 1/312; G01N 2035/00752; G01N 2035/0096; G01N 35/04; G01T 7/12; A61B 2562/0295; A61B 2562/08; A61B 5/14532; A61B 5/14546; A61B 5/1455; A61B 90/90
USPC .............................................. 378/42, 44, 45
See application file for complete search history.

(56) References Cited

U.S. PATENT DOCUMENTS

| | | | |
|---|---|---|---|
| 8,065,094 B2 * | 11/2011 | Statham | 378/44 |
| 2001/0021240 A1 * | 9/2001 | Kojima | G01N 23/04 378/45 |
| 2007/0224083 A1 * | 9/2007 | Ouchi | G01N 21/253 422/64 |
| 2012/0267440 A1 * | 10/2012 | Nakaya | G01N 1/312 235/494 |

FOREIGN PATENT DOCUMENTS

JP 2008-008856 A 1/2008

* cited by examiner

*Primary Examiner* — Irakli Kiknadze
(74) *Attorney, Agent, or Firm* — Banner & Witcoff, Ltd.

(57) ABSTRACT

A sample plate is for X-ray analysis to which a sample is fixed in performing an analysis using an X-ray fluorescent analyzer, and includes: a plate-like body that supports the sample; and a code-indicated portion provided on the plate-like body in which information on the sample is encoded and indicated.

7 Claims, 4 Drawing Sheets

X-RAY FLOURESCENT ANALYZER

CROSS-REFERENCE TO RELATED APPLICATION

This application claims priority from Japanese Patent Application No. 2014-140234, filed on Jul. 8, 2014, the entire subject matter of which is incorporated herein by reference.

BACKGROUND

1. Technical Field

The present invention relates to a sample plate for X-ray analysis and an X-ray fluorescent analyzer that are used for measurement of a sample such as a standard material in performing a fluorescent X-ray analysis in which toxic substances can be detected and which is used for screening products and the like.

2. Description of the Related Art

In a fluorescent X-ray analysis, a sample is irradiated with X-rays emitted from an X-ray tube, fluorescent X-rays emitted from the sample are detected by an X-ray detector, and a qualitative analysis of a composition of the sample or a quantitative analysis of a concentration, a film thickness, or the like is performed based on a relationship between intensities of the X-rays. Since samples can be rapidly analyzed in a non-destructive manner by the fluorescent X-ray analysis, the fluorescent X-ray analysis is widely used in the fields of process control, quality control, and the like. In recent years, high precision and high sensitivity of the fluorescent X-ray analysis are achieved, and thus trace measurement is enabled. In particular, the fluorescent X-ray analysis is expected to be spread as an analysis method of detecting toxic substances contained in materials, complex electronic parts, or the like.

Generally, when a quantitative elemental analysis is performed using an X-ray fluorescent analyzer, a standard material is measured plural times, and a relation between intensities of fluorescent X-rays and concentrations of elements needs to be calibrated based on a calibration curve (for example, see JP-A-2008-008856). Since the intensity from even the same standard material varies with an aging variation of the apparatus, the standard material needs to be periodically re-measured, and the calibration curve needs to be updated such that a quantitatively-measured concentration of an unknown sample is not changed.

The above-described technique in the related art has the following problems.

A user periodically performs a task of measuring plural standard materials in order to update the calibration curve as described above. This task has problems in that it may become highly cumbersome to a user and an error of misidentifying the samples may easily be made when there are a large number of standard materials. In addition, since unevenness in concentration value occurs in manufacturing a standard material, a target concentration cannot be completely realized. For example, even when a standard material is manufactured with a target concentration of 100 ppm, the standard material may have a concentration of 101 ppm or 99 ppm. In manufacturing the standard material, the standard material is labeled with the actually-measured value. However, in order to configure a calibration curve on software of the apparatus, the user may have to manually input the uneven concentration as a result. Depending on standard materials, there is a case in which the same standard material is used for plural calibration curves. In this case, if the same value is not input two or more times, all the calibration curves may not be updated. Since the standard materials to be measured in updating the calibration curves are almost uniform, the task may become tedious to the user. Even if there is an input error, the apparatus may have no means for automatically detecting the error in situ, and thus a calibration curve allowing wrong analysis values to be output may be created and used. Therefore, a method of reducing an operator's load and reducing an error is desired.

SUMMARY

The present disclosure has been made in view of the above-described circumstances, and one of objects of the present disclosure is to provide a sample plate for X-ray analysis and an X-ray fluorescent analyzer capable of improving workability of measuring a sample in a fluorescent X-ray analysis and suppressing occurrence of an error.

According to an exemplary embodiment of the present disclosure, there is provided a sample plate for X-ray analysis to which a sample is fixed in performing an analysis using an X-ray fluorescent analyzer. The sample plate for X-ray analysis is provided with: a plate-like body that supports the sample; and a code-indicated portion provided on the plate-like body in which information on the sample is encoded and indicated.

According to another exemplary embodiment of the present disclosure, there is provided an X-ray fluorescent analyzer provided with: an X-ray tube that irradiates a sample with a primary X-ray; a detector that detects a fluorescent X-ray emitted from the sample irradiated with the primary X-ray; a sample stage on which the sample plate for X-ray analysis according to the exemplary embodiment is installed; an imaging unit that captures image of the code-indicated portion; and a code processor that decodes the information encoded in the code-indicated portion based on the image of the code-indicated portion captured by the imaging unit.

BRIEF DESCRIPTION OF THE DRAWINGS

The above and other aspects of the present disclosure will become more apparent and more readily appreciated from the following description of illustrative embodiments of the present disclosure taken in conjunction with the attached drawings, in which.

DETAILED DESCRIPTION

Hereinafter, a sample plate for X-ray analysis and an X-ray fluorescent analyzer according to an embodiment of the invention will be described with reference to FIGS. 1A to 3.

Figure 1A:
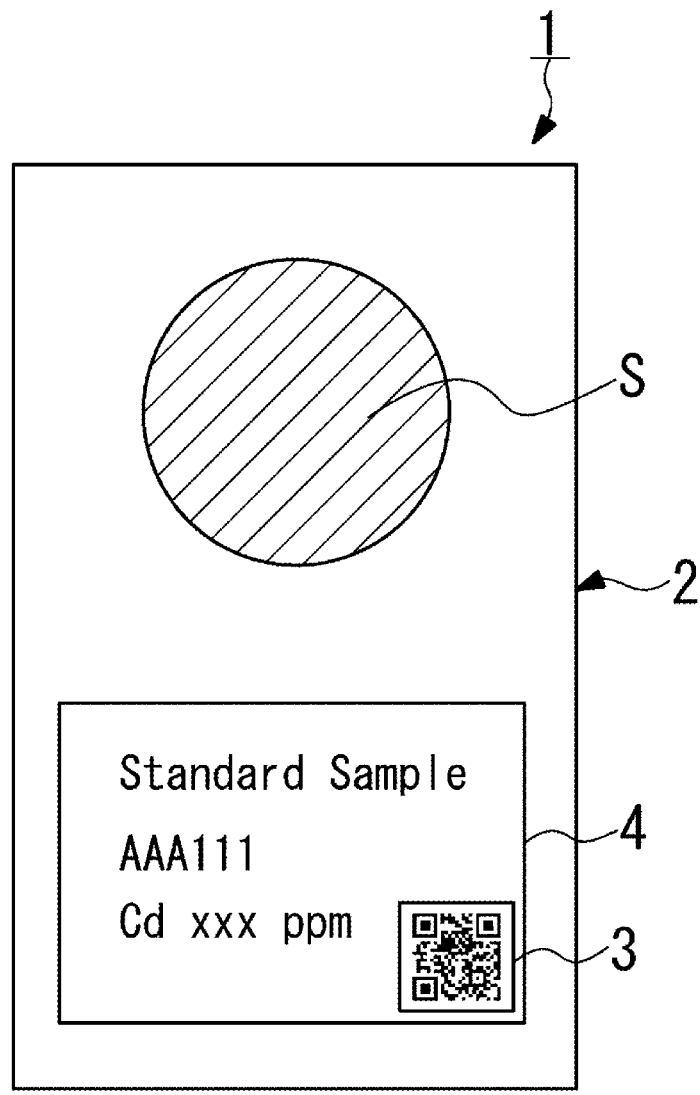
FIGS. 1A and 1B are a plan view and a bottom diagram illustrating a sample plate for X-ray analysis according to an embodiment of the invention, respectively.
Figure 1B:
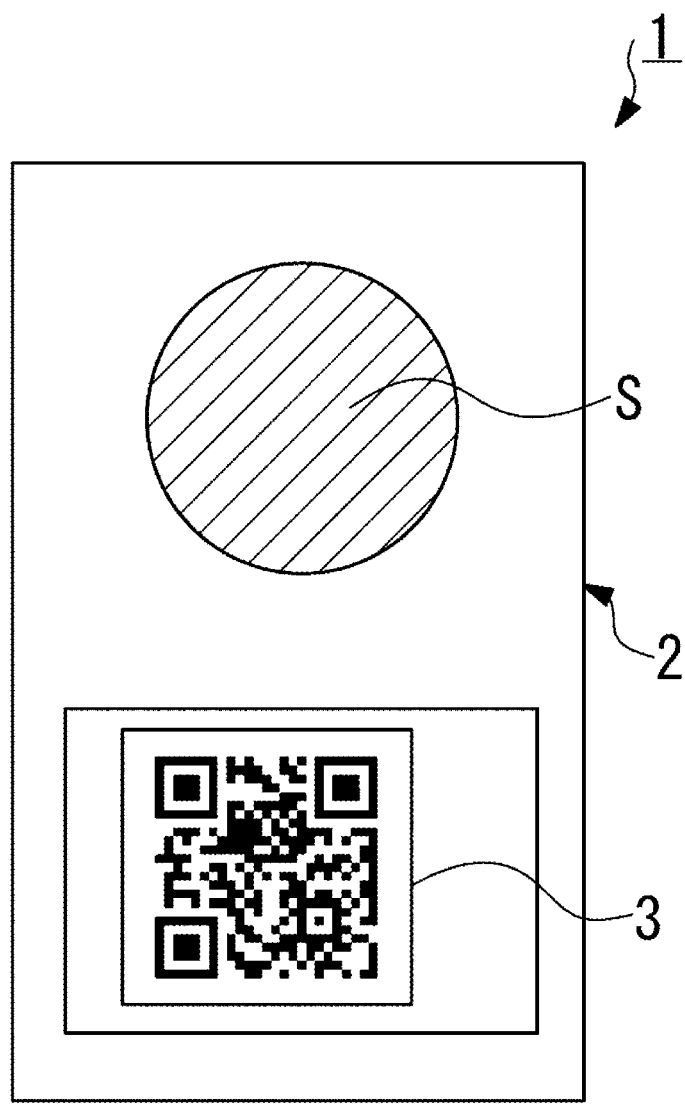
Figure 2:
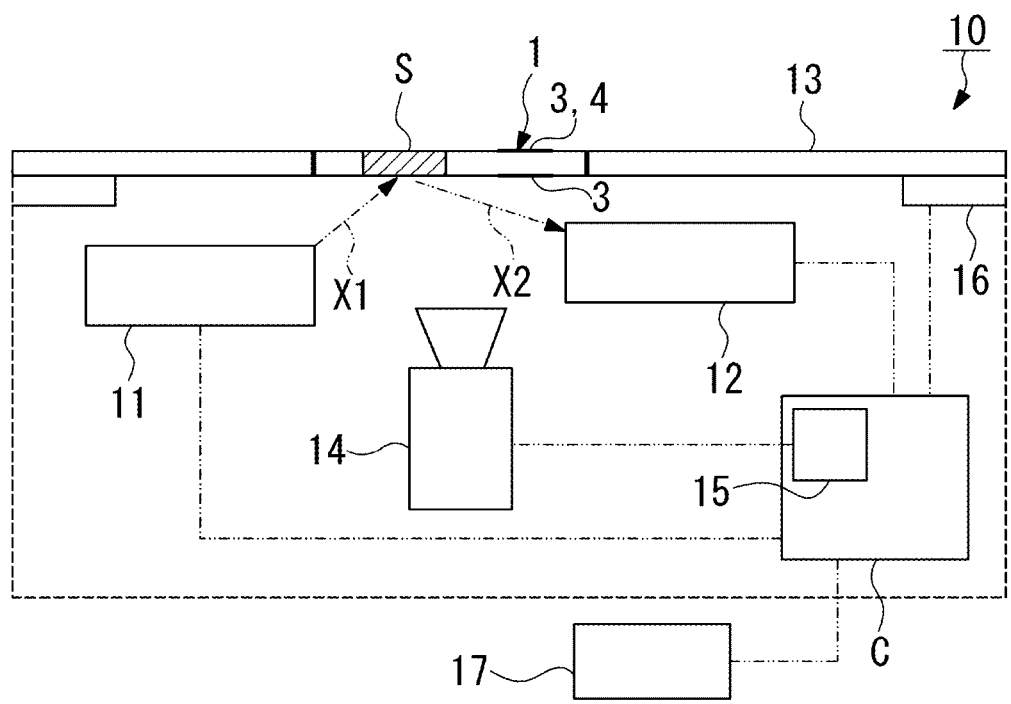
FIG. 2 is a diagram illustrating the entire configuration of the X-ray fluorescent analyzer according to the embodiment.

As illustrated in FIG. 2, a sample plate for X-ray analysis 1 according to the embodiment is a sample plate for X-ray analysis to which a sample S is fixed in performing an analysis using an X-ray fluorescent analyzer 10, and the sample plate for X-ray analysis includes the sample S and a plate-like body 2 that supports the sample S as illustrated in FIGS. 1A and 1B.

The plate-like body 2 has a code-indicated portion 3 in which at least information on the sample S is encoded and indicated.

The code-indicated portion 3 is indicated on both the front and rear surfaces of the plate-like body 2. The code-indicated portion 3 on the front surface is indicated in an information-described area 4 of the plate-like body 2. Identification character strings such as information indicating that the sample S is a standard material, element names of the sample, and a sample number are indicated in the information-described area 4.

The identification character strings and the code-indicated portion 3 of the information-described area 4 may be printed as a label, and the label may be attached to the plate-like body 2.

The sample S is formed in a disc shape which is fitted into a circular hole in an upper portion of the plate-like body 2 having a rectangular shape.

The code-indicated portion 3 is indicated as a two-dimensional code which is called a QR code (registered trademark). Although the two-dimensional code is preferred, a barcode which is a one-dimensional code may be employed as the code-indicated portion 3.

The code-indicated portion 3 is located at a position which is separated by a certain distance at a certain angle from the position of the sample S fitted into the plate-like body 2.

When the sample S is a standard material used for performing a quantitative elemental analysis, the code-indicated portion 3 includes element concentration information of the standard material. When the sample S is a standard material used for a quantitative elemental analysis, the code-indicated portion 3 includes information indicating that the sample is a standard material.

When the sample S is a thickness standard foil used for performing film-thickness measurement, the code-indicated portion 3 includes thickness information of the thickness standard foil.

In addition to the above-described concentration information or thickness information, the code-indicated portion 3 may include a variety of encoded information such as information indicating that the sample S is a standard material, element names of the sample S, identification character strings such as a sample number (serial number), manufacturing date and time, expiration date, and a composition ratio of elements.

As illustrated in FIG. 2, the X-ray fluorescent analyzer 10 according to the embodiment includes an X-ray tube 11 that irradiates the sample S with a primary X-ray X1, a detector 12 that detects a fluorescent X-ray X2 emitted from the sample S irradiated with the primary X-ray X1, a sample stage 13 on which the sample plate for X-ray analysis 1 is disposed, an imaging unit 14 that images the code-indicated portion 3, a code processor 15 that decodes the encoded information of the code-indicated portion 3 based on the code-indicated portion 3 imaged by the imaging unit 14, a sample stage moving mechanism 16 that is capable of moving the sample stage 13, a controller C that controls the sample stage moving mechanism 16, and a display device 17 that is capable of displaying an image captured by the imaging unit 14 or various types of information.

The X-ray fluorescent analyzer 10 is a bottom-irradiation type X-ray fluorescent analyzer that irradiates the sample S with the primary X-ray X1 from the bottom side (rear surface side) of the sample plate for X-ray analysis 1.

The controller C controls the movement of the sample stage 13 using the sample stage moving mechanism 16 and moves the sample S of the sample plate for X-ray analysis 1 to an X-ray irradiation area XA of the primary X-ray X1 depending on the position of the code-indicated portion 3 imaged by the imaging unit 14.

The controller C controls the display device 17 and displays a warning on the display device 17 when the information indicating that the sample is a standard material is not included in the information decoded by the code processor 15 in measuring the element concentration of the standard material.

The X-ray tube 11 is an X-ray tube capable of emitting the primary X-ray X1 and serves to emit X-rays, which are generated by accelerating thermoelectrons e generated from a filament (cathode) in the tube by a voltage applied between the filament (cathode) and a target (anode) 2b and causing the thermoelectrons to collide with W (tungsten), Mo (molybdenum), Cr (chromium), or the like as the target, as the primary X-ray X1 from a window formed of a beryllium foil or the like.

The detector 12 is provided with a semiconductor detection device (for example, a Si (silicon) device which is a pin-structure diode) (not illustrated) and is set to generate electric charges corresponding to one X-ray photon when the one X-ray photon is incident and to output a voltage signal including information of energy of the X-ray photon and an incidence timing from a preamplifier connected to the rear end of the detector.

The imaging unit 14 is configured by a sample-observing camera such as a CCD for specifying a position on which measurement is performed through the irradiation with the primary X-ray X1. The center of a captured image becomes a measurement point. The imaging unit 14 transmits the captured image to the controller C and the code processor 15.

The sample stage moving mechanism 16 is a motor-driven stage that drives in three axes of X, Y, and Z. The X and Y directions are the horizontal directions, and the Z direction is the vertical direction.

The controller C may be configured by a computer including a CPU and the like which is connected to the X-ray tube 11, the detector 12, the sample stage moving mechanism 16, the imaging unit 14, and the display device 17 so as to control these units.

The X-ray fluorescent analyzer 10 according to the embodiment may also be provided with an analyzer (not illustrated) that is connected to the detector 12 so as to analyze a signal from the detector 12. The analyzer may be a pulse height analyzer (multi-channel pulse height analyzer) that acquires a height of a voltage pulse from the signal and generates an energy spectrum.

The method of reading the information of the sample S using the X-ray fluorescent analyzer 10 according to the embodiment will be described below with reference to an example in which a standard material is measured.

Figure 3:
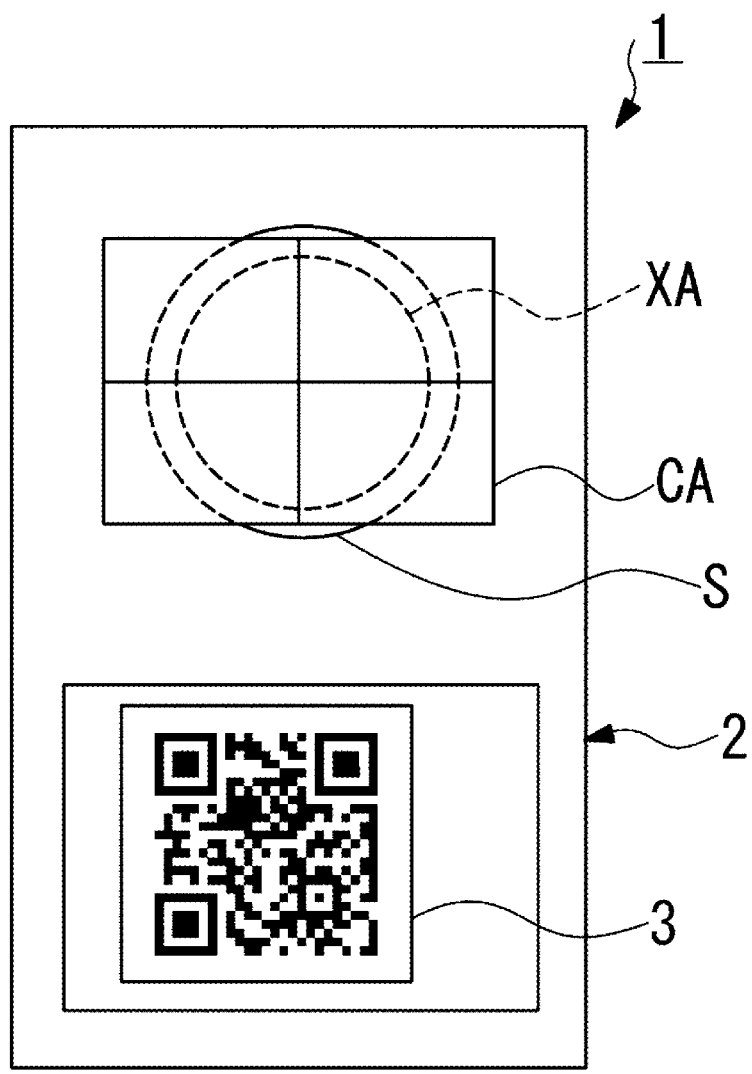
FIG. 3 is a diagram illustrating a field of view of a camera and an irradiation area of an X-ray beam in the embodiment.

First, an operator installs the sample plate for X-ray analysis 1, to which a sample S of a standard material to be measured is fixed, on the sample stage 13 and locates the code-indicated portion 3 by operating the sample stage moving mechanism 16 under the control of the controller C so that the code-indicated portion 3 is included in a field of view CA of the imaging unit 14. When the sample S and the code-indicated portion 3 are not included in the same field of view CA, the sample stage 13 is automatically moved to a measurement point in a relative movement manner by measuring the position of the code-indicated portion 3 using the imaging unit 14, and then the measurement is performed. That is, when the measurement executing operation is performed, the controller C reads the position and the angle of the code-indicated portion 3 with respect to the sample S based on the image of the code-indicated portion 3 captured by the imaging unit 14 and controls the sample stage moving mechanism 16 so as to move the sample stage 13, such that X-ray irradiation area XA is automatically moved to the measurement point as illustrated in FIG. 3.

The code processor 15 decodes the encoded information of the code-indicated portion 3 based on the captured image of the code-indicated portion 3 and reads a variety of information such as the element concentration information and the identification character strings included therein, and the controller C displays the read information on the display device 17. The controller C uses the read information as information for identifying data to be updated in a stored standard material table or producing a calibration curve. At this time, when it is determined that the same standard material is used for plural calibration curves based on the identification character strings of the standard material included in the code-indicated portion 3, the plural calibration curves can be updated by one-time measurement.

When the information indicating that the sample is a standard material is not included in the decoded information, the controller C displays on the display device 17 a warning indicating that the sample plate for X-ray analysis 1 of the sample S which is not a standard material is erroneously set. At this time, a warning sound may be generated simultaneously.

In this manner, in the sample plate for X-ray analysis 1 according to the embodiment, since the plate-like body 2 has the code-indicated portion 3 in which the at least information on the sample S is encoded and indicated, it is possible to automatically read the information on the sample S by imaging the code-indicated portion 3 using the imaging unit 14 on the apparatus side and decoding the captured image.

In particular, since the code-indicated portion 3 is indicated as a two-dimensional code, the code-indicated portion can include much more information than a one-dimensional code such as a barcode.

Since the code-indicated portion 3 includes the element concentration information of a standard material, the element concentration information which is obtained by actually measuring concentration unevenness in manufacturing the standard material can be automatically read into the apparatus and it is thus possible to easily create and update the calibration curve.

When the code-indicated portion 3 includes thickness information of a thickness standard foil, it is possible to automatically read the thickness information of the thickness standard foil into the apparatus.

Since the X-ray fluorescent analyzer 10 according to the embodiment includes the code processor 15 that decodes the information of the code-indicated portion 3 encoded based on the code-indicated portion 3 imaged by the imaging unit 14, it is possible to automatically read the information on the sample S of the sample plate for X-ray analysis 1 into the apparatus.

Since the controller C moves the sample stage 13 using the sample stage moving mechanism 16 and moves the sample S of the sample plate for X-ray analysis 1 to the X-ray irradiation area XA of the primary X-ray X1 depending on the position of the code-indicated portion 3 imaged by the imaging unit 14, it is possible to perform alignment by automatically moving the sample S to the X-ray irradiation area XA using the code-indicated portion 3 as an alignment marker.

The controller C displays a warning on the display device 17 when the information indicating that the sample is a standard material is not included in the information decoded by the code processor 15 in measuring the element concentration of the standard material. Accordingly, even when a sample plate for X-ray analysis 1 other than the sample plate for X-ray analysis 1 of the standard material is erroneously set for analysis, it is possible to prevent an error by causing the controller C to display a warning.

The scope of the invention is not limited to the above-described embodiment, and the invention can be modified in various forms without departing from the spirit of the invention.

For example, in the above-described embodiment, the invention is applied to an energy-dispersion type X-ray fluorescent analyzer that measures energy and intensity of an X-ray using a pulse height analyzer. However, the invention may be applied to a wavelength-dispersion type X-ray fluorescent analyzer that disperses a fluorescent X-ray using a dispersive crystal and measures a wavelength and intensity of the X-ray.

Although the imaging unit has a narrow field of view and cannot simultaneously image the code-indicated portion and the sample, an image unit having a wide field of view capable of simultaneously imaging the code-indicated portion and the sample may be employed.

Although the above-described code-indicated portion is printed and attached as a label, the code-indicated portion may be indicated on the plate-like body using any method such as a laser marking method which has no influence on fluorescent X-rays.

The X-ray irradiation area and the code-indicated portion may be simultaneously included in a single field of view in a mirror optical system.

As described in the above with reference to the embodiment of the present invention, the present invention has the following advantages.

In the sample plate for X-ray analysis and the X-ray fluorescent analyzer according to the invention, since the plate-like body has the code-indicated portion in which the at least information on the sample is encoded and indicated, it is possible to automatically read the information on the sample by imaging the code-indicated portion using the imaging unit on the apparatus side and decoding the code-indicated portion using the apparatus or the like. Therefore, it is possible to reduce an operator's burden of inputting concentration values in newly purchasing samples such as standard materials or updating the calibration curves thereof, and it is possible to prevent occurrence of an error. In addition, since a standard material of a redundant calibration curve does not need to be repetitively measured, it is possible to shorten a working time.

What is claimed is:

1. An X-ray fluorescent analyzer comprising:
   an X-ray tube that irradiates a sample with a primary X-ray;
   a detector that detects a fluorescent X-ray emitted from the sample irradiated with the primary X-ray;
   a sample stage on which a sample plate for X-ray analysis is installed, the sample plate including:
      a plate-like body that supports the sample; and
      a code-indicated portion provided on the plate-like body in which information on the sample is encoded and indicated;

an imaging unit that captures an image of the code-indicated portion; and a code processor that operates to:
  decode the information encoded in the code-indicated portion based on the image of the code-indicated portion captured by the imaging unit; and
  update a calibration curve based on the decoded information.

2. The X-ray fluorescent analyzer according to claim 1 further comprising:
  a sample stage moving mechanism that moves the sample stage; and
  a controller that controls the sample stage moving mechanism,
  wherein the controller controls the sample stage moving mechanism to move the sample stage and the sample supported by the sample plate to an X-ray irradiation area of the primary X-ray based on a position of the code-indicated portion determined from the image captured by the imaging unit.

3. The X-ray fluorescent analyzer according to claim 2 further comprising:
  a display device that displays various types of information,
  wherein when the sample is a standard material used for performing a quantitative elemental, the code-indicated portion includes information indicating that the sample is the standard material, and
  wherein the controller controls the display device to display a warning when the information indicating that the sample is a standard material is not included in the information decoded by the code processor in measuring an element concentration of the standard material.

4. The X-ray fluorescent analyzer according to claim 1, wherein the code-indicated portion is indicated as a two-dimensional code.

5. The X-ray fluorescent analyzer according to claim 1, wherein when the sample is a standard material used for performing a quantitative elemental analysis, the code-indicated portion includes information indicating element concentration of the standard material.

6. The X-ray fluorescent analyzer according to claim 1, wherein when the sample is a thickness standard foil used for performing film thickness measurement, the code-indicated portion includes information indicating thickness of the thickness standard foil.

7. The X-ray fluorescent analyzer according to claim 1, wherein the code-indicated portion is provided on both front and rear faces of the plate-like body.

* * * * *